United States Patent [19]
Audousset

[11] Patent Number: 6,093,220
[45] Date of Patent: *Jul. 25, 2000

[54] COMPOSITIONS FOR THE OXIDATION DYEING OF KERATIN FIBRES AND DYEING PROCESS

[75] Inventor: Marie-Pascale Audousset, Asnieres, France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/896,636

[22] Filed: Jul. 18, 1997

[30] Foreign Application Priority Data

Jul. 19, 1996 [FR] France ................................. 96 09107

[51] Int. Cl.⁷ ..................................................... A61K 7/13
[52] U.S. Cl. ......................... 8/412; 8/408; 8/409; 8/416; 8/421; 8/423
[58] Field of Search ................ 8/406, 408, 409, 8/410, 412, 416, 421, 423

[56] References Cited

U.S. PATENT DOCUMENTS

| | | |
|---|---|---|
| 5,421,833 | 6/1995 | Lorenz ........................................ 8/410 |
| 5,494,489 | 2/1996 | Akram et al. ................................. 8/408 |
| 5,500,021 | 3/1996 | Cotteret et al. .............................. 4/408 |
| 5,525,123 | 6/1996 | Lorenz et al. ............................... 8/408 |

FOREIGN PATENT DOCUMENTS

| | | |
|---|---|---|
| 27 39 227 | 3/1978 | Germany . |
| 27 14 831 | 10/1978 | Germany . |
| 44 08 506 | 9/1995 | Germany . |
| 464 448 | 12/1968 | Switzerland . |

OTHER PUBLICATIONS

Chemical Abstracts, vol. 87, No. 10, Sep. 5, 1977, entry No. 87: 73239r.
Chemical Abstracts, vol. 83, No. 18, Nov. 3, 1975, p. 322.
English Derwent Abstract of DE 27 39 227, Mar. 1978.
English Derwent Abstract of DE 27 14 831, Oct. 1978.
English Derwent Abstract of DE 44 08 506, Sep. 1995.

*Primary Examiner*—Caroline D. Liott
*Attorney, Agent, or Firm*—Finnegan, Henderson, Farabow, Garrett & Dunner, L.L.P.

[57] ABSTRACT

A composition for the oxidation dyeing of keratin fibres, preferably comprising 2-amino-3-hydroxypyridine as first coupler in combination with an oxidation base chosen from para-phenylenediamines of formula (I) and/or para-aminophenols of formula (II), as well as a second coupler chosen from meta-aminophenol derivatives of formula (III), as well as to the dyeing process using this composition with an oxidizing agent.

28 Claims, No Drawings

COMPOSITIONS FOR THE OXIDATION DYEING OF KERATIN FIBRES AND DYEING PROCESS

The present invention relates to a composition for the oxidation dyeing of keratin fibres, in particular human keratin fibres such as the hair, comprising 2-amino-3-hydroxypyridine as first coupler in combination with a suitably selected oxidation base, as well as a suitably selected meta-aminophenol derivative as second coupler, as well as to the dyeing process using this composition with an oxidizing agent.

It is known to dye keratin fibres, and in particular human hair, with dye compositions containing oxidation dye precursors, in particular ortho- or para-phenylenediamines, ortho- or para-aminophenols, which are generally referred to as oxidation bases. The oxidation dye precursors, or oxidation bases, are colourless or weakly coloured compounds which, when combined with oxidizing products, may give rise to coloured compounds and dyes by a process of oxidative condensation.

It is also known that the shades obtained with these oxidation bases may be varied by combining them with couplers or coloration modifiers, the latter being chosen in particular from aromatic meta-diamines, meta-aminophenols, meta-diphenols and certain indole compounds such as 4-hydroxyindole.

The variety of molecules used as oxidation bases and couplers makes it possible to obtain a wide range of colours.

The so-called "permanent" coloration obtained by means of these oxidation dyes seeks to satisfy a certain number of requirements. Thus, it is desired to have no toxicological drawbacks and to allow shades of the desired intensity to be obtained and to have good staying power with respect to external agents (light, bad weather, washing, permanent-waving, perspiration and rubbing).

It is also desired that the dyes allow white hairs to be covered and, lastly, to be as unselective as possible, that is to say to allow the smallest possible differences in coloration to be produced over the entire length of the same keratin fibre, which may indeed be differently sensitized (i.e. damaged) between its tip and its root.

Compositions for the oxidation dyeing of keratin fibres, containing 2-amino-3-hydroxypyridine as first coupler in combination with an oxidation base such as para-toluylenediamine, and meta-aminophenol as second coupler, have already been proposed, in particular in German patent application DE 4,408,506. However, such compositions are not entirely satisfactory, in particular regarding the intensity of the colorations obtained.

Compositions for the oxidation dyeing of keratin fibres, containing a specific oxidation base, namely 2-(2'-hydroxyethyl)amino-5-aminobenzene, in combination with 2-methyl-5-aminophenol and 2-amino-3-hydroxypyridine as couplers, have also been proposed, in particular in U.S. Pat. No. 5,421,833. Such compositions are not entirely satisfactory either, in particular regarding the staying power of the colorations obtained with respect to perspiration and the above-mentioned external agents.

Now, the inventor has just discovered that it is possible to obtain novel dyes that are particularly fast, especially to perspiration, light and shampooing, by combining 2-amino-3-hydroxypyridine as first coupler, at least one suitably selected oxidation base and a suitably selected meta-aminophenol as second coupler.

This discovery forms the basis of the present invention.

The subject of the invention is thus a composition for the oxidation dyeing of keratin fibres, and in particular of human keratin fibres such as the hair, characterized in that it comprises, in a medium which is suitable for dyeing:

at least one first coupler selected from 2-amino-3-hydroxypyridine and acid addition salts thereof, at least one oxidation base selected from
(i) para-phenylenediamines of formula (I) below and acid addition salts thereof:

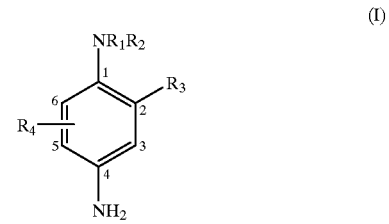

wherein:
$R_1$ represents a hydrogen atom or a $C_1$–$C_4$ alkyl, $C_1$–$C_4$ monohydroxyalkyl, $C_2$–$C_4$ polyhydroxyalkyl, alkoxy($C_1$–$C_4$)alkyl, phenyl or 4'-aminophenyl radical, $R_2$ represents a hydrogen atom or a $C_1$–$C_4$ alkyl, $C_1$–$C_4$ monohydroxyalkyl or $C_2$–$C_4$ polyhydroxyalkyl radical, $R_3$ represents a hydrogen atom, a halogen atom such as a chlorine atom, or a $C_1$–$C_4$ alkyl, $C_1$–$C_4$ monohydroxyalkyl or $C_1$–$C_4$ hydroxyalkoxy radical, $R_4$ represents a hydrogen atom or a $C_1$–$C_4$ alkyl radical, with the proviso that:
when $R_2$ represents a β-hydroxyethyl radical and when $R_1$ and $R_4$ represent a hydrogen atom, then $R_3$ is other than a methyl radical,
when $R_2$ represents a β-hydroxyethyl radical and when $R_1$ and $R_3$ represent a hydrogen atom, then $R_4$ cannot represent a methyl radical in position 6, and (ii) para-aminophenols of formula (II) below and acid addition salts thereof:

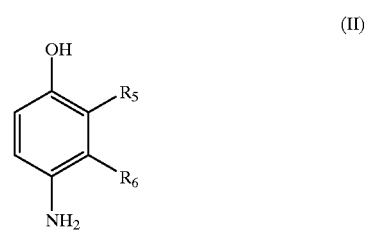

wherein:
$R_5$ represents a hydrogen atom or a $C_1$–$C_4$ alkyl, $C_1$–$C_4$ monohydroxyalkyl, alkoxy($C_1$–$C_4$)alkyl or $C_1$–$C_4$ aminoalkyl radical, $R_6$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, cyano($C_1$–$C_4$)alkyl or alkoxy ($C_1$–$C_4$)alkyl radical, with the proviso that at least one of the radicals $R_5$ or $R_6$ represents a hydrogen atom, and at least one second coupler selected from meta-aminophenols of formula (III) below and acid addition salts thereof:

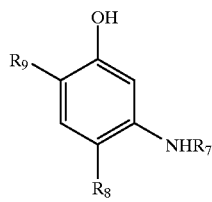

wherein:
R$_7$ represents a hydrogen atom or a C$_1$–C$_4$ alkyl, C$_1$–C$_4$ monohydroxyalkyl or C$_2$–C$_4$ polyhydroxyalkyl radical,
R$_8$ represents a hydrogen atom, a C$_1$–C$_4$ alkyl or C$_1$–C$_4$ alkoxy radical or a halogen atom selected from chlorine, bromine and fluorine, and
R$_9$ represents a hydrogen atom or a C$_1$–C$_4$ alkyl, C$_1$–C$_4$ alkoxy, C$_1$–C$_4$ monohydroxyalkyl, C$_2$–C$_4$ polyhydroxyalkyl, C$_1$–C$_4$ monohydroxyalkoxy or C$_2$–C$_4$ polyhydroxyalkoxy radical,
is wherein at least one of the radicals R$_7$, R$_8$ and R$_9$ is other than a hydrogen atom.

As demonstrated by the examples below, the colorations obtained with the composition in accordance with the invention are of good dyeing power and have excellent properties of fastness both with respect to atmospheric agents such as light and bad weather and with respect to perspiration and the various treatments to which the hair may be subjected (washing, permanent-waving). These properties are particularly noteworthy, especially regarding the fastness of the colorations obtained with respect to perspiration, light and shampooing.

The subject of the invention is also a process for the oxidation dyeing of keratin fibres using this composition.

The addition salts with an acid which may be used in the context of the dye compositions of the invention (bases and couplers) are chosen in particular from hydrochlorides, hydrobromides, sulphates and tartrates.

Among the para-phenylenediamines of formula (I) above, mention may be made more particularly of para-phenylenediamine, para-toluylenediamine, 2-n-propyl-para-phenylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 1,β-methoxyethylamino-4-aminobenzene, and the addition salts thereof with an acid.

Among the para-aminophenols of formula (II) above, mention may be made more particularly of para-aminophenol, 3-methyl-4-aminophenol, 3-fluoro-4-aminophenol, 3-hydroxymethyl-4-aminophenol, 2-methyl-4-aminophenol, 2-hydroxymethyl-4-aminophenol, 2-methoxymethyl-4-aminophenol, 2-aminomethyl-4-aminophenol and 2-(β-hydroxyethylaminomethyl)-4-aminophenol, and the addition salts thereof with an acid.

Among the meta-aminophenols of formula (III) above, mention may be made more particularly of 5-amino-2-methoxyphenol, 5-amino-2-(β-hydroxyethyloxy)-phenol, 5-amino-2-methylphenol, 5-N-(β-hydroxyethyl)-amino-2-methylphenol, 5-N-(β-hydroxyethyl)amino-4-methoxy-2-methylphenol, 5-amino-4-methoxy-2-methyl-phenol, 5-amino-4-chloro-2-methylphenol, 5-amino-2,4-dimethoxyphenol and 5-(γ-hydroxypropylamino)-2-methylphenol, and the addition salts thereof with an acid.

The 2-amino-3-hydroxypyridine and/or the addition salt or salts of this compound with an acid preferably represent from 0.0001 to 10% by weight approximately relative to the total weight of the dye composition, and even more preferably from 0.005 to 7% by weight approximately.

The oxidation bases in accordance with the invention, that is to say the para-phenylenediamine(s) of formula (I) and/or the para-aminophenol(s) of formula (II), together preferably represent from 0.0005 to 10% by weight approximately relative to the total weight of the dye composition, and even more preferably from 0.01 to 7% by weight approximately.

The meta-aminophenol(s) of formula (III) in accordance with the invention preferably represent from 0.0001 to 5% by weight approximately relative to the total weight of the dye composition, and even more preferably from 0.001 to 3% by weight approximately.

The appropriate medium for the dyeing (or the support) generally comprises water or a mixture of water and at least one organic solvent to solubilize the compounds which would not be sufficiently soluble in water. Organic solvents which may be mentioned, for example, are C$_1$–C$_4$ lower alkanols such as ethanol and isopropanol; glycerol; glycols and glycol ethers such as 2-butoxyethanol, propylene glycol, diethylene glycol monoethyl ether and monomethyl ether, and aromatic alcohols such as benzyl alcohol or phenoxyethanol, similar products and mixtures thereof.

The solvents may be present in proportions preferably ranging approximately from 1 to 40% by weight relative to the total weight of the dye composition, and even more preferably ranging approximately from 5 to 30% by weight.

The pH of the dye composition as defined above is generally approximately from 5 to 12. It may be adjusted to the desired value using acidifying or basifying agents usually used in the dyeing of keratin fibres.

Among the acidifying agents which may be mentioned, by way of example, are inorganic or organic acids such as hydrochloric acid, orthophosphoric acid, carboxylic acids such as tartaric acid, citric acid and lactic acid, and sulphonic acids.

Among the basifying agents which may be mentioned, by way of example, are aqueous ammonia, alkaline carbonates, alkanolamines such as mono-, di- and triethanolamines as well as the derivatives thereof, sodium hydroxide, potassium hydroxide and the compounds of formula (IV) below:

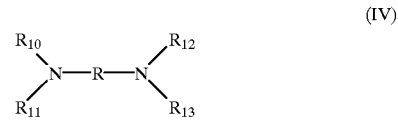

in which R is a propylene residue optionally substituted with a hydroxyl group or a C$_1$–C$_4$ alkyl radical; R$_{10}$, R$_{11}$, R$_{12}$ and R$_{13}$, which may be identical or different, represent a hydrogen atom or a C$_1$–C$_4$ alkyl or C$_1$–C$_4$ hydroxyalkyl radical.

The dye composition in accordance with the invention may also contain, in addition to the dyes defined above, couplers other than 2-amino-3-hydroxy-pyridine and meta-aminophenols of formula (III) and the addition salts thereof with an acid and/or oxidation bases other than the para-phenylenediamines of formula (I), para-aminophenols of formula (II) and the addition salts thereof with an acid and/or direct dyes, in particular in order to modify the shades or to enrich them with glints.

The dye composition according to the invention may also include various adjuvants used conventionally in compositions for dyeing the hair, such as anionic, cationic, nonionic, amphoteric or zwifterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

Obviously, a person skilled in the art will take care to select the optional complementary compound(s) mentioned above such that the advantageous properties intrinsically associated with the dye composition according to the invention are not, or are not substantially, adversely affected by the addition or additions envisaged.

The dye composition according to the invention may be in various forms, such as in the form of liquids, creams, gels or any other form which is suitable for dyeing keratin fibres, and in particular human hair.

The subject of the invention is also a process for dyeing keratin fibres, and in particular human keratin fibres such as the hair, using the dye composition as defined above.

According to this process, the dye composition as defined above is applied to the fibres, the colour being developed at acidic, neutral or alkaline pH using an oxidizing agent which is added, only at the time of use, to the dye composition or which is present in an oxidizing composition that is applied simultaneously or sequentially in a separate manner.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is preferably left in place for 3 to 40 minutes approximately, more preferably 5 to 30 minutes approximately, after which the fibres are rinsed, washed with shampoo, rinsed again and dried.

The oxidizing agent present in the oxidizing composition as defined above may be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibres preferably ranges approximately from 2 to 12 and even more preferably from 5 to 11. It is adjusted to the desired value using acidifying or basifying agents usually used in the dyeing of keratin fibres and as defined above.

The oxidizing composition as defined above may also include various adjuvants used conventionally in compositions for dyeing the hair and as defined above.

The composition which is finally applied to the keratin fibres may be in various forms, such as in the form of liquids, creams, gels or any other form which is suitable for dyeing keratin fibres, and in particular human hair.

Another subject of the invention is a multi-compartment device for dyeing or dyeing "kit" or any other multi-compartment packaging system, a first compartment of which contains the dye composition as defined above and a second compartment of which contains the oxidizing composition as defined above. These devices may be equipped with a means which makes it possible to apply the desired mixture to the hair, such as the devices described in patent FR-2,586,913 in the name of L'Oréal, the disclosure of which is specifically incorporated by reference herein.

The examples which follow are intended to illustrate the invention without, however, limiting the scope thereof.

EXAMPLES

Examples 1 and 2

The following dye compositions in accordance with the invention were prepared (contents in grams):

| EXAMPLE | 1 | 2 |
|---|---|---|
| Para-toluylenediamine sulphate (oxidation base) | 0.434 | — |
| Para-toluylenediamine (oxidation base) | — | 1.0 |
| 2-Amino-3-hydroxypyridine (first coupler) | 0.11 | 0.5 |
| 2-Methyl-5-aminophenol (second coupler) | 0.123 | 0.56 |
| Common dye support (*) | (*) | (*) |
| Water q.s. | 100 g | 100 g |
| (*) common dye support: | | |
| - Oleyl alcohol polyglycerolated with 2 mol of glycerol | 4.0 g | |
| - Oleyl alcohol polyglycerolated with 4 mol of glycerol, containing 78% active material (A.M.) | | |
| - Oleic acid | 5.69 g A.M. | |
| - Oleylamine containing 2 mol of ethylene oxide, sold under the tradename Ethomeen O12 by the company Akzo | 3.0 g | |
| - Diethylaminopropyl laurylaminosuccinamate, sodium salt containing 55% A.M. | 7.0 g | |
| - Oleyl alcohol | 3.0 g A.M. | |
| - Oleic acid diethanolamide | 5.0 g | |
| - Propylene glycol | 12.0 g | |
| - Ethyl alcohol | 3.5 g | |
| - Dipropylene glycol | 7.0 g | |
| - Propylene glycol monomethyl ether | 0.5 g | |
| - Sodium metabisulphite as an aqueous solution containing 35% A.M. | 9.0 g | |
| - Ammonium acetate | 0.455 g A.M. | |

Each dye composition was mixed, at the time of use, with an equal amount of an oxidizing composition of 20-volumes aqueous hydrogen peroxide solution (6% by weight) having a pH of about 3.

Each mixture obtained had a pH of about 10.2 and was applied for 30 minutes to locks of natural or permanent-waved grey hair containing 90% white hairs. The locks of hair were rinsed, washed with a standard shampoo and then dried.

The locks of hair were dyed in the shades shown in the table below:

| EXAMPLE | SHADE ON NATURAL HAIR | SHADE ON PERMANENT-WAVED HAIR |
|---|---|---|
| 1 | Iridescent mahogany | Muted pink |
| 2 | Mahogany | Slightly muted deep purple |

Comparative Examples 3 and 4

The following dye compositions were prepared (contents in grams):

| EXAMPLE | 3(**) | 4 |
|---|---|---|
| Para-toluylenediamine sulphate (oxidation base) | — | 0.434 |
| 4-Amino-1-N-(β-hydroxyethyl)amino-2-methylbenzene sulphate dihydrate (oxidation base) | 0.609 | — |
| 2-Amino-3-hydroxypyridine (first coupler) | 0.11 | 0.11 |
| 2-Methyl-5-aminophenol (second coupler) | 0.123 | 0.123 |
| Common dye support (*) | (*) | (*) |
| Water q.s. | 100 g | 100 g |

(*) common dye support:
This is identical to that used in Examples 1 and 2 above.
(**): example not forming part of the invention It is important to note that the above dye compositions contain the same molar amount of oxidation base, namely $2 \times 10^{-3}$ mol.

Each dye composition was mixed, at the time of use, with an equal amount of an oxidizing composition of 20-volumes aqueous hydrogen peroxide solution (6% by weight) and having a pH of about 3.

Each mixture obtained had a pH of about 10.2 and was applied to locks of natural grey hair containing 90% white hairs according to the dyeing process described above in Examples 1 and 2.

The locks thus dyed were then subjected to a test of light fastness (Xenotest).

To do this, the locks of dyed hair were fixed on a support (cardboard or plastic). These supports were then arranged on sample holders which were rotated about a xenon lamp for a duration of 40 hours under a relative humidity level of 25±5% and at a temperature of 42.5±2.5° C.

The colour of the locks was evaluated in the Munsell system, before and after the light fastness test, using a Minolta CM 2002 colorimeter.

According to the Munsell notation, a colour is defined by the expression H V/C in which the three parameters respectively denote the shade or Hue (H), the intensity or Value (V) and the purity or Chromaticity (C), the oblique line in this expression simply being a convention and not indicating a ratio.

The difference in colour of each lock before and after the light fastness test reflects the degradation of the coloration due to the action of light, and was calculated by applying the Nickerson formula:

$$\Delta E = 0.4 \ Co\Delta H + 6\Delta V + 3\Delta C,$$

as described, for example, in "Couleur, Industrie et Technique"; pages 14–17; Vol. No. 5; 1978.

In this formula, ΔE represents the difference in colour between two locks, ΔH, ΔV and ΔC represents the variation in absolute value of the parameters H, V and C, and Co represents purity of the lock relative to which it is desired to evaluate the difference in colour (purity of the lock before the test).

| EX-AMPLE | Colour before the test | Colour after the test | Degradation of the coloration | | | |
|---|---|---|---|---|---|---|
| | | | ΔH | ΔV | ΔC | ΔE |
| 3(**) | 8.6 RP 3.7/1.8 | 4.9 R 4.3/1.7 | 6.3 | 0.6 | 0.1 | 8.4 |
| 4 | 4.5 R 3.5/2.6 | 7.0 R 3.5/2.5 | 2.5 | 0 | 0.1 | 2.9 |

(**): example not forming part of the invention

It is observed that the coloration obtained with the dye composition of Example 4 containing a combination, in accordance with the invention, of 2-amino-3-hydroxypyridine, 2-methyl-5-aminophenol and para-toluylenediamine (para-phenylenediamine of formula (I)) is much better at withstanding the action of light than the coloration obtained with the dye composition of Example 3 not forming part of the invention since it contains the combination of 2-amino-3-hydroxypyridine, 2-methyl-5-aminophenol and 4-amino-1-N-(β-hydroxyethyl)amino-2-methylbenzene which is a compound not corresponding to formula (I) of the para-phenylenediamines defined above, and which is described, for example, in U.S. Pat. No. 5,421,833.

I claim:

1. A composition for the oxidation dyeing of keratin fibres comprising, in a medium which is suitable for dyeing:

at least one first coupler wherein said first coupler is 2-amino-3-hydroxypyridine or an acid addition salt thereof, at least one oxidation base wherein said oxidation base is
   (i) a para-phenylenediamine of formula (I) below or an acid addition salt thereof:

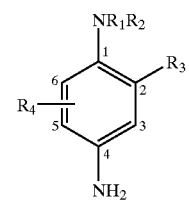

(I)

wherein:

$R_1$ represents a hydrogen atom or a $C_1$–$C_4$ alkyl, $C_1$–$C_4$ monohydroxyalkyl, $C_2$–$C_4$ polyhydroxyalkyl, alkoxy($C_1$–$C_4$)alkyl, phenyl or 4'-aminophenyl radical, $R_2$ represents a hydrogen atom or a $C_1$–$C_4$ alkyl, $C_1$–$C_4$ monohydroxyalkyl or $C_2$–$C_4$ polyhydroxyalkyl radical, $R_3$ represents a hydrogen atom, a halogen atom, or a $C_1$–$C_4$ alkyl, $C_1$–$C_4$ monohydroxyalkyl or $C_1$–$C_4$ hydroxyalkoxy radical, $R_4$ represents a hydrogen atom or a $C_1$–$C_4$ alkyl radical, with the proviso that:

when $R_2$ represents a β-hydroxyethyl radical and when $R_1$ and $R_4$ represent a hydrogen atom, then $R_3$ is other than a methyl radical, when $R_2$ represents a β-hydroxyethyl radical and when $R_1$ and $R_3$ represent a hydrogen atom, then $R_4$ cannot represent a methyl radical in position 6, or (ii) a para-aminophenol of formula (II) below or an acid addition salt thereof:

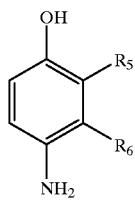

(II)

wherein:
  $R_5$ represents a hydrogen atom or a $C_1$–$C_4$ alkyl, $C_1$–$C_4$ monohydroxyalkyl, alkoxy($C_1$–$C_4$)alkyl or $C_1$–$C_4$ aminoalkyl radical,
  $R_6$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, cyano($C_1$–$C_4$) alkyl or alkoxy($C_1$–$C_4$)alkyl radical, with the proviso that at least one of the radicals $R_5$ or $R_6$ represents a hydrogen atom, and
at least one second coupler wherein said second coupler is a meta-aminophenol of formula (III) below or an acid addition salt thereof:

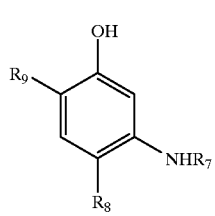

(III)

wherein:
  $R_7$ represents a hydrogen atom or a $C_1$–$C_4$ alkyl, $C_1$–$C_4$ monohydroxyalkyl or $C_2$–$C_4$ polyhydroxyalkyl radical,
  $R_8$ represents a hydrogen atom, a $C_1$–$C_4$ alkyl or $C_1$–$C_4$ alkoxy radical or a halogen atom wherein said halogen is chlorine, bromine or fluorine, and
  $R_9$ represents a hydrogen atom or a $C_1$–$C_4$ alkyl, $C_1$–$C_4$ alkoxy, $C_1$–$C_4$ monohydroxyalkyl, $C_2$–$C_4$ polyhydroxyalkyl, $C_1$–$C_4$ monohydroxyalkoxy or $C_2$–$C_4$ polyhydroxyalkoxy radical,
wherein at least one of the radicals $R_7$, $R_8$ and $R_9$ is other than a hydrogen atom.

2. A composition according to claim 1 wherein said keratin fibres are human keratin fibres.

3. A composition according to claim 2 wherein said human keratin fibres are hair.

4. A composition according to claim 1 wherein said $R_3$ of formula (I) is a chlorine atom.

5. A composition according to claim 1, wherein said para-phenylenediamine of formula (I) is para-phenylenediamine, para-toluylenediamine, 2-n-propyl-para-phenylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 1,β-methoxyethylamino-4-aminobenzene, an acid addition salt thereof, or a mixture thereof.

6. A composition according to claim 1 wherein said para-aminophenol of formula (II) is para-aminophenol, 3-methyl-4-aminophenol, 3-fluoro-4-aminophenol, 3-hydroxymethyl-4-aminophenol, 2-methyl-4-aminophenol, 2-hydroxymethyl-4-aminophenol, 2-methoxymethyl-4-aminophenol, 2-aminomethyl-4-aminophenol, 2-(β-hydroxyethylaminomethyl)-4-aminophenol, an acid addition salt thereof, or a mixture thereof.

7. A composition according to claim 1 wherein said meta-aminophenol of formula (III) is 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylpheneol, an acid addition salt thereof, or a mixture thereof.

8. A composition according to claim 1 wherein said acid addition salts are hydrochlorides, hydrobromides, sulphates or tartrates.

9. A composition according to claim 1 wherein said at least one first coupler represents from 0.0001 to 10% by weight relative to the total weight of the dye composition.

10. A composition according to claim 9 wherein said at least one first coupler represents from 0.005 to 7% by weight relative to the total weight of the dye composition.

11. A composition according to claim 1 wherein said at least one oxidation base represents from 0.0005 to 10% by weight relative to the total weight of the dye composition.

12. A composition according to claim 11, wherein said at least one oxidation base represents 0.01 to 7% by weight relative to the total weight of the dye composition.

13. A composition according to claim 1 wherein said at least one second coupler represents from 0.0001 to 5% by weight relative to the total weight of the dye composition.

14. A composition according to claim 13 wherein said at least one second coupler represents from 0.001 to 3% by weight relative to the total weight of the dye composition.

15. A composition according to claim 1 wherein said medium which is suitable for dyeing comprises water.

16. A composition according to claim 15 wherein said medium comprises a mixture of water and at least one organic solvent, wherein said solvent is a $C_1$–$C_4$ lower alkanol, glycerol, glycol, glycol ether, an aromatic alcohol or a mixture thereof.

17. A composition according to claim 1 wherein said composition has a pH ranging from 5 to 12.

18. A composition according to claim 1 wherein said composition further contains at least one additional coupler or oxidation base other than 2-amino-3-hydroxypyridine or an acid addition salt thereof, the paraphenylenediamines of formula (I) or acid addition salts thereof, the paraaminophenols of formula (II) or acid addition salts thereof, or the meta-aminophenols of formula (III) or acid addition salts thereof.

19. A process for dyeing keratin fibres comprising applying to said fibres a composition according to claim 1 and developing color at acidic, neutral or alkaline pH by applying an oxidizing agent to said fibres.

20. A process according to claim 19 wherein said oxidizing agent is combined with said composition and immediately thereafter said composition and said oxidizing agent are applied to said fibres.

21. A process according to claim 19 wherein said oxidizing agent is applied to said fibres after said composition is applied to said fibres.

22. A process according to claim 19 wherein said oxidizing agent is applied to said fibres and thereafter said composition is applied to said fibres.

23. A process according to claim 19 wherein said oxidizing agent and said composition are separately and simultaneously applied to said fibres.

24. A process according to claim 19 wherein said keratin fibres are human keratin fibres.

25. A process according to claim 24 wherein said human keratin fibres are hair.

26. A process according to claim 19 wherein said oxidizing-agent is hydrogen peroxide, urea peroxide, an alkali metal bromate or a persalt.

27. A process according to claim 26 wherein said persalt is a perborate or a persulphate.

28. A multi-compartment device or a multi-compartment dyeing kit comprising a first compartment containing a dye composition according to claim 1, and a second compartment containing an oxidizing agent.

* * * * *